United States Patent [19]

McKay et al.

[11] Patent Number: 4,902,849
[45] Date of Patent: Feb. 20, 1990

[54] DEHYDROGENATION PROCESS

[75] Inventors: Dwight L. McKay, Bartlesville, Okla.; Michael E. Olbrich, Lake Jackson, Tex.

[73] Assignee: Phillips Petroleum Company, Bartlesville, Okla.

[21] Appl. No.: 307,122

[22] Filed: Feb. 6, 1989

[51] Int. Cl.$^4$ .............................................. C07C 5/333
[52] U.S. Cl. .................................... 585/660; 585/661; 502/50
[58] Field of Search .................. 585/660, 661; 502/50

[56] References Cited

U.S. PATENT DOCUMENTS

| | | | |
|---|---|---|---|
| 2,671,763 | 3/1954 | Winstrom et al. | 502/50 |
| 2,867,579 | 1/1959 | Loughran et al. | 502/50 |
| 2,886,515 | 5/1959 | Turkevich | 208/134 |
| 3,011,967 | 11/1959 | Schmitkons et al. | 502/50 |
| 3,230,179 | 1/1966 | Schwarzenbek | 502/50 |
| 3,315,007 | 4/1967 | Abell, Jr. | 585/660 |
| 3,461,183 | 8/1969 | Hepp et al. | 585/660 |
| 3,641,182 | 2/1972 | Box et al. | 260/680 R |
| 3,670,044 | 6/1972 | Drehman et al. | 260/683.3 |
| 3,684,698 | 1/1971 | Hallman | 502/50 |
| 3,880,776 | 4/1975 | Box et al. | 252/466 PT |
| 3,894,110 | 7/1975 | Drehman | 260/680 R |
| 3,957,688 | 5/1976 | Farha et al. | 252/455 R |
| 4,003,852 | 1/1977 | Hayes | 252/466 PT |
| 4,048,244 | 9/1977 | Hayes | 260/668 D |
| 4,152,365 | 5/1979 | Drehman | 585/256 |
| 4,206,035 | 6/1980 | Hutson et al. | 208/65 |
| 4,542,248 | 9/1985 | Lucien | 585/661 |
| 4,551,574 | 11/1985 | Imai et al. | 585/661 |
| 4,613,715 | 9/1986 | Haskell | 585/412 |
| 4,665,267 | 5/1987 | Barri | 585/661 |
| 4,752,595 | 6/1988 | McCullen et al. | 502/50 |

Primary Examiner—Patrick P. Garvin
Assistant Examiner—E. D. Irzinski
Attorney, Agent, or Firm—K. K. Brandes

[57] ABSTRACT

In a process for dehydrogenating alkanes containing 2-5 carbon atoms per molecule in the presence of steam and a catalyst composition comprising IIA and/or IIB metal aluminate, a noble metal and a Group IVA metal oxide, the improvement comprises the step of contacting the catalyst composition, after it has been oxidatively regenerated, with a reducing gas comprising free hydrogen and steam.

16 Claims, No Drawings

DEHYDROGENATION PROCESS

BACKGROUND OF THE INVENTION

This invention relates to a process for dehydrogenating light paraffins. In another aspect, this invention relates to the use of a promoted zinc aluminate catalyst in a dehydrogenation process.

It is known to dehydrogenate light aliphatic hydrocarbons in the presence of catalysts which comprise Group II metal aluminate, a Group IVA metal oxide and a Group VIII metal. However, there is an ever present need to improve conversion and selectivity to desired products in dehydrogenation processes. The process of this invention is directed to attaining these improvements.

SUMMARY OF THE INVENTION

It is an object of this invention to dehydrogenate light paraffins (alkanes) in the presence of a promoted Group II metal aluminate catalyst. It is another object of this invention to pretreat a regenerated catalyst before it is used again in the dehydrogenation process, so as to enhance conversion and/or selectivity. Other objects and advantages will become apparent from the disclosure and the appended claims.

In accordance with this invention, a process for dehydrogenating light alkanes comprises the steps of:

(a) contacting a feed stream comprising at least one alkane (paraffin) having from 2 to 5 carbon atoms per molecule in a reactor with steam and a catalyst composition comprising (i) at least one aluminate spinel selected from the group consisting of aluminates of Group IIA metals and Group IIB metals of the Periodic Table (defined in Webster's New Collegiate Dictionary, 1977, page 852), (ii) at least one metal selected from the group consisting of nickel, ruthenium, rhodium, palladium, osmium, iridium and platinum and (iii) at least one compound of a metal selected from the group consisting of germanium, tin and lead, under such dehydrogenation conditions as to at least partially convert said at least one alkane to at least one alkene (monoolefin);

(b) discontinuing the flow of the hydrocarbon feed stream through the reactor containing the catalyst composition, and passing a purge gas stream selected from the group consisting of steam, inert gases (such as $N_2$, Ar, He and the like) and mixtures of steam and at least one inert gas through the reactor, so as to substantially remove hydrocarbon feed from the reactor;

(c) thereafter contacting the catalyst composition in the reactor with steam and a free oxygen containing gas stream, under such regeneration conditions as to substantially burn off carbonaceous deposits (coke) on the catalyst composition and to obtain a regenerated catalyst composition;

(d) discontinuing the flow of the free oxygen containing gas stream through the reactor and passing a purge gas stream, as described in step (b), through the reactor, so as to substantially remove free oxygen from the reactor;

(e) contacting the regenerated catalyst composition in the reactor with a reducing gas stream comprising free hydrogen and stream so as to obtain a reactivated catalyst composition, i.e., a catalyst composition having higher dehydrogenation activity than the regenerated catalyst composition obtained in step (c); and (f) discontinuing the flow of free hydrogen, and contacting the above-described alkane-containing feed stream in the reactor with steam and the reactivated catalyst composition obtained in step (e) under such dehydrogenation conditions, as have been recited in step (a), as to at least partially convert said at least one alkane to at least one alkene.

In a preferred embodiment, the alkane-containing feed stream is essentially free of added hydrogen gas and oxygen gas and consists essentially of at least one alkane. Essentially no hydrogen gas and no oxygen gas are added to the reactor in steps (a) and (f). In another preferred embodiment, the aluminate spinel component of the catalyst composition is zinc aluminate, the Group VIII metal component of the catalyst composition is platinum, and the Group IVA metal component of the catalyst composition is tin oxide (more preferably $SnO_2$). In still once (i.e., once or twice or more than twice).

DETAILED DESCRIPTION OF THE INVENTION

The dehydrogenation catalyst composition which is employed in the process of this invention can be prepared by any suitable method and in any suitable manner, such as those well known in the art. The preparation comprises combining, in any suitable manner, (i) a Group IIA metal aluminate spinel (i.e., aluminate spinel of Be and/or Mg and/or Ca and/or Sr and/or Ba) or a Group IIB metal aluminate spinel (i.e., aluminate spinel of Cd and/or Zn), or a mixture of two or more of the above metal aluminate spinels; (ii) Group VIII metal and/or compound(s) thereof, and (iii) compound(s) of Ge and/or Sn and/or Pb.

Aluminate spinels, as referred to herein, are compounds of the formula $M(AlO_2)_2$ or $MOAl_2O_3$, wherein M is a metal of Group IIA or IIB of the Periodic Table (as defined in Webster's New Collegiate Dictionary, 1977, page 852) with a valence of 2, such as Zn, Mg, Be, Ca and the like. The preparation of these aluminate spinels is described in numerous patents, such as U.S. Patent No. 3,641,182; 3,670,044; 3,880,776; 3,894,110; 3,957,688 and 4,152,365, the disclosure of which are herein incorporated by reference. In a preferred embodiment, tin oxide is incorporated into the aluminate spinel. In another preferred embodiment, component (i) comprises zinc aluminate as major component and calcium aluminate as binder (generally present at about 5–25 weight-%).

In the presently preferred method of preparation, the metal aluminate is prepared by ball-milling appropriate amounts of zinc oxide and alumina and, optionally, tin oxide (SnO and/or $SnO_2$), and calcining (preferably by heating in air) the mixture at a sufficiently high temperature for a sufficient length of time to form the spinel. Preferably, the spinel component is used as support material, which is impregnated with component (ii) and with component (iii) in any suitable manner, either sequentially in any order or simultaneously, as has been described in the above-cited patents.

The components of the catalyst composition generally are present at the following levels: about 80–89 weight-% of Group IIA and/or IIB metal aluminate spinel (preferably zinc aluminate); about 0.05-5 weight-% of Group VIII metal (preferably Pt); and about 0.1-5 weight-% Group IVA metal (preferably Sn, present as oxide. It is understood that additional components which are beneficial for catalyzing the dehydrogenation of saturated hydrocarbons may also be present in small amounts, such as Re, Au, Ag, alkali metal, Ce, and the like. Suitable inorganic binder materials (such as amorphous alumina) may also be present. Generally the surface area of the composition of matter (after calcination) is in the range of from about 5 to about 100 m$^2$/g (determined by nitrogen adsorption in accordance with the BET method).

Any suitable paraffin containing 2-5 carbon atoms per molecule (normal alkane or isoalkane, or mixtures) can be used as feed in the dehydrogenation process of this invention, i.e., in steps (a) and (f). Non-limiting examples are ethane, propane, n-butane, isobutane, n-pentane, 2-methylbutane, and the like. Particularly preferred are propane, n-butane and isobutane; at present, isobutane is most preferred.

The dehydrogenation condition of the process in steps (a) and (f) of the invention are well known and have been described in the above-cited patents. Stream is present to alleviate coke deposition on the catalyst, to retard catalyst deactivation, and to enhance feed conversion. The reaction temperature in steps (a) and (f) is considerably higher than the normal boiling temperature (measured at 1 atm.) of the feed alkane. The reaction temperature generally is in the range of from about 500 to about 650° C. The molar ratio (essentially equal to volume ratio) of steam to alkane in the vaporized feed generally is in the range of from about 0.5:1 to about 30:1 (preferably from about 2:1 to about 10:1) The pressure generally is in the range of from about 0 to about 200 psig, and preferably is about 20-100 psig.

In the dehydrogenation steps, generally a mixture of steam and vaporized alkane is preheated and passed through a reactor (or a train of two or more reactors in series or in parallel) containing a fixed bed of the catalyst composition of this invention ( which can be in any suitable form, such as granules, pellets, spheres and the like). The gas hourly space velocity of the vaporized alkane feed (excluding steam) generally is in the range of from about 100 to about 10,000 cc alkane per cc catalyst per hour, preferably from about 500 to about 2,000 cc/cc/hour. The flow rate of steam is determined by the desired volume ratio of steam to alkane feed (as disclosed above). Free oxygen is substantially absent during dehydrogenation steps (a) and (f) of this invention since $O_2$ causes the formation of higher amounts of undesirable carbon oxides (CO and/or $CO_2$) during the process.

The catalyst composition of this invention gradually loses some of its catalytic activity during the dehydrogenation process. When the catalytic activity has dropped below an effective level (generally after about 6-20 hours on stream), the flow of the alkane-containing feed is cut off, and a purge gas (steam and/or inert gas) is passed through the catalyst bed (preferably at a temperature of about 500°-650° C., for about 1-60 minutes) in step (b), so as substantially remove hydrocarbons from the reactor.

Then the catalyst composition is regenerated in step (c). This catalyst regeneration step is preferably carried out by treating the catalyst for a suitable time with a stream of steam-diluted air, as is shown in U.S. Pat. No. 4,613,715, the disclosure of which is herein incorporated by reference. Generally, the regeneration temperature in step (c) is in the range of from about 450 to about 750° C. (preferably about 500°-700° C.), and the molar ratio of steam to free oxygen is in the range of from about 40:1 to about 200:1. The flow rate of steam is approximately the same as in step (a). The pressure during the regeneration cycle generally is about 0-200 psig, preferably about 20-100 psig. The duration of the regeneration step depends on the regeneration conditions and on the amount of coke deposits to be removed. Generally, the regeneration step is carried out for about 0.1 to about 5 hours, preferably about 0.2-1 hour. If an inert gas is used in preceding step (b), generally the flow of this inert gas is reduced or discontinued in step (c).

Thereafter, the flow of the free oxygen containing gas stream is discontinued, and a purge gas (described above) is passed through the reactor, in step (d), at conditions essentially the same as those described for step (b).

Thereafter, the reactivation (pretreating step (e) is carried out with a gas mixture comprising free hydrogen and steam. Any suitable pretreating conditions can be employed. The flow rate of steam is about the same as in step (a). Generally, the molar ratio of steam to hydrogen is in the range of from about 0.5:1 to 100:1, preferably from about 2:1 to about 20:1. Generally, the hydrogen flow is in the range of from about 100 to about 1,000 cc/cc/hour. The duration of step (e) generally is about 1 to about 60 minutes, preferably about 2-20 minutes, and the temperature generally is about 450°-650° C. When an inert gas has been used in preceding purge step (d), generally the flow of this inert gas is reduced or dicontinued.

The hydrogen-pretreated, regenerated catalyst composition which is more active (in terms of feed conversion and generally also in terms of selectivity to desired monoolefins) than the regenerated catalyst obtained in step (c) can then be re-employed in dehydrogenation process step (f). The dehydrogenation process conditions of this step (f) are essentially the same as those in step (a), described above. The dehydrogenation, regeneration, purging and $H_2$-pretreating steps can be repeated as many times as desirable and feasible.

The product of the dehydrogenation steps of the process of this invention process comprises monoolefins (alkenes). Preferably, these monoolefinic hydrocarbons are the principal reaction products. By-produces are O, $CO_2$, diolefins, and possibly aromatics. When propane is used as feed, primarily propylene is formed; when n-butane is used as feed, primarily butene-1 and butene-2 are formed; and when isobutane is used as feed, primarily isobutene is formed.

The formed monoolefinic hydrocarbons can be recovered, after having been separated from other components of the reaction product mixture of the dehydrogenationprocess and from unconverted feed by any suitable means, such as fractional distillation (preferably at low temperature and high pressure), well known absorption/desorption processes, and membrane separation techniques. Unreacted hydrocarbon feed, after it has been substantially separated from reaction product components, can be recycled to the dehyrogenation reactor which contains the catalyst composition.

The following examples are presented in further illustration of the invention and are not to be considered as unduly limiting the scope of this invention.

EXAMPLE

This example illustrates the dehydrogenation of isobutane over a promoted zinc aluminate catalyst, with and without prior treatment of the catalyst with hydrogen.

Isobutane and steam were introduced into a pilot plant reactor having a length of about 2 ft. and a diameter of about 2 inches. The reactor was filled with a layer (about 14 inches high) containing 974 grams (780 cc) of a dehydrogenation catalyst comprising zinc aluminate. The catalyst was prepared substantially in accordance withe the method described in Example I of U.S. Patent 4,152,365, and contained about 44.0 weight-% ZnO, 53.5 weight-% $Al_2O_3$, 1.3 weight-% $SnO_2$ and 0.6 weight-% Pt.

Liquid isobutane was introduced into the reactor at a feed rate of 3077 cc/hr (1728 g/hr), and steam was introduced at a rate of about 2125 g/hr. Thus, the weight ratio of steam to isobutane was 1.23:1, and the molar ratio of steam to isobutane was 3.95:1. The liquid hourly space velocity of isobutane was 3.94 cc/cc catalyst/hour, which translated to a gas hourly space velocity at S.T.P. conditions of about 890 cc/cc/ catalyst/hour. The average temperature of the catalyst bed was about 1070° F., and the average reaction pressure was about 50 psig.

Generally, the mixture of isobutane and steam was passed through the reactor for 7 hours, at about 1070° F. Then the isobutane flow was discontinued, the reactor was purged with steam (2125 g/hr) for 5 minutes, and air was introduced into the reactor for 2 minutes at a rate of about 10 standard cubic feed per hour (SCFH) and then for 25 minutes at about 20 SCFH (while the steam flow rate remained about 2125 g/hour), so as to regenerate the hot catalyst (i.e., to burn off coke deposits). thereafter, the flow of air was discontinued, and pure steam was passed through the reactor for 5 minutes, before isobutane was introduced again for another 7 hour dehydrogenation cycle. In the invention run, hydrogen gas, mixed with steam at a molar (volume) ratio of steam to $H_2$ of 9:1, was passed through teh datalyst bed, at about 1070° F., for 10 minutes (after the above-described regeneration step and steam purge step), before the isobutane flow was started again.

The reactor effluent was cooled to room temperature (about 77° F.), and the uncondensed (i.e., gaseous) portion of the effluent was analyzed by gas chromatography. The main component of the uncondensed effluent was isobutene. Test results for runs, with and without $H_2$ treatment of the regenerated dehydrogenation catalyst bed (as described above), are summarized in Table I.

TABLE I

| Run | $H_2$ Pre-Treatment | Run Time (Hours) | % Isobutane Conversion | % Selectivity to Isobutene |
| --- | --- | --- | --- | --- |
| 1 (Control) | No | 1.3 | 56.0 | 87.5 |
| | | 1.9 | 55.1 | 89.2 |
| | | 2.5 | 54.0 | 90.2 |
| | | 3.1 | 52.4 | 91.1 |
| | | 3.6 | 51.3 | 91.4 |
| | | 4.2 | 50.5 | 91.9 |
| | | 4.8 | 49.0 | 92.8 |
| | | 5.3 | 48.1 | 93.1 |
| | | 5.9 | 46.7 | 93.6 |
| | | 6.5 | 46.1 | 93.5 |
| | | Average: | 50.9 | 91.4 |
| 2 (Invention) | Yes | 1.0 | 58.2 | 84.4 |
| | | 1.6 | 57.2 | 87.1 |
| | | 2.1 | 56.2 | 88.2 |
| | | 2.7 | 55.1 | 89.4 |
| | | 3.3 | 54.5 | 90.1 |
| | | 3.8 | 54.0 | 90.3 |
| | | 4.4 | 53.2 | 90.7 |
| | | 5.0 | 52.5 | 91.2 |
| | | 5.5 | 51.7 | 91.9 |
| | | 6.1 | 51.2 | 91.9 |
| | | 6.7 | 50.8 | 92.0 |
| | | Average: | 54.1 | 89.7 |

Test results in Table I indicate that the average isobutane conversion was about 6% higher in invention run 2 than in control run 1. The average isobutene yield of invention run 2, with hydrogen pretreatment of the catalyst, was $54.1 \times 89.7 \div 100 = 48.5\%$; whereas the average isobutene yield of control run 1, without hydrogen pretreatment of the catalyst, was $50.9 \times 91.4 \div 100 = 46.5\%$. Thus, hydrogen pretreatment of the dehydrogenation catalyst resulted in a significant increase of the isobutene yield.

Reasonable variations, modifications and adaptations for various usages and conditions can be made within the scope of the disclosure and the appended claims, without departing from the scope of this invention.

That which is claimed is:

1. A process for dehydrogenating light alkanes comprising the steps of:
    (a) contacting a feed stream comprising at least one alkane having from 2 to 5 carbon atoms per molecule in a reactor with steam and a catalyst composition comprising (i) at least one aluminate spinel selected from the group consisting of Group IIA metal aluminates and Group IIB metal aluminates, (ii) at least one metal selected from the group consisting of nickel, ruthenium, rhodium, palladium, osmium, iridium and platinum, and (iii) at least one compound of a metal selected from the group consisting of germanium, tin and lead, under such dehydrogenation conditions as to at least partially convert said at least one alkane to at least one alkene;
    (b) discontinuing the flow of said feed stream through said reactor containing said catalyst composition, and passing a purge gas stream selected from the group consisting of steam, at least one inert gas and mixtures of steam and at least one inert gas through said reactor, so as to substantially remove hydrocarbons from said reactor;
    (c) thereafter contacting said catalyst composition in said reactor, with steam and a free oxygen containing gas stream, under such regeneration conditions as to substantially burn off carbonaceous deposits on said catalyst composition and to obtain a regenerated catalyst composition;
    (d) discontinuing the flow of the free oxygen containing gas stream through said reactor containing said regenerated catalyst composition, and passing a purge gas stream, as described in step (b), through said reactor so as to substantially remove free oxygen from said reactor;
    (e0 contacting said regenerated catalyst composition in said reactor with a reducing gas stream comprising free hydrogen and steam, under such conditions as to obtain a reactivated catalyst composition, wherein the molar ratio of steam to free hydrogen in said reducing gas stream is in the range of from about 2:1 to about 20:1; and
    (f) discontinuing the flow of free hydrogen through said reactor and contacting said feed stream in said reactor with steam and the reactivated catalyst composition obtained in step (e), under such dehydrogenation conditions as to at least partially convert said at least one alkane to at least one alkene.

2. A process in accordance with claim 1, wherein said at least one alkane is selected from the group consisting of propane, n-butane and isobutane.

3. A process in accordance with claim 1, wherein said catalyst composition comprises zinc aluminate, platinum and tin oxide.

4. A process in accordance with claim 3, wherein said catalyst composition additionally comprises calcium aluminate.

5. A process in accordance with claim 1, wherein said catalyst composition comprises about 0.05-5 weight-% Pt and about 0.1-5 weight-% Sn, present as tin oxide.

6. A process in accordance with claim 1, wherein said dehydrogenation conditions in steps (a) and (f) comprise a temperature in the range of from about 500° to about 650° C. and a molar ratio of steam to alkane in the range of from 0.5:1 to about 30:1.

7. A process in accordance with claim 6, wherein essentially hydrogen gas and no oxygen gas are added to said reactor in steps (a) and (f).

8. A process in accordance with claim 1, wherein steam is used as purge gas stream in step (b).

9. A process in accordance with claim 1, wherein said regeneration conditions in steps (c) comprise a temperature in the range of from about 450° to about 750° C. and a molar ratio of steam to free oxygen in the range of from about 40:1 to about 200:1.

10. A process in accordance with claim 1, wherein steam is used as purge gas in step (d).

11. A process in accordance withe claim 1, wherein reducing step (e) is carried out at a temperature in the range of from about 450 to about 650° C., for a time period in the range of from about 1 to about 60 minutes.

12. A process in accordance with claim 1, wherein said reducing gas stream used in step (e) consists essentially of free hydrogen and steam.

13. A process in accordance with claim 1, wherein steps (b) through (f) are repeated at least once.

14. A process in accordance with claim 1, wherein said at least one alkene obtained in steps (a) and (f) is selected from the group consisting of propylene, butene-1, butene-2 and isobutene.

15. A process in accordance with claim 1, wherein said at least one alkene obtained in steps (a) and (f) is recovered.

16. A process in accordance with claim 1, wherein said catalyst composition consists essentially of components (i), (ii), and (iii).

* * * * *

UNITED STATES PATENT AND TRADEMARK OFFICE
CERTIFICATE OF CORRECTION

PATENT NO. : 4,902,849

DATED : February 20, 1990

INVENTOR(S) : Dwight L. McKay and Michael E. Olbrich

It is certified that error appears in the above-identified patent and that said Letters Patent is hereby corrected as shown below:

Claim 1, column 6, line 58, delete "(eO" and substitute therefor --- (e) ---.

Claim 7, column 7, line 21, insert --- no --- between "essentially" and "hydrogen".

Claim 11, column 8, line 7, delete "withe" and substitute therefor --- with ---.

Signed and Sealed this

Ninth Day of April, 1991

Attest:

HARRY F. MANBECK, JR.

*Attesting Officer*

Commissioner of Patents and Trademarks